United States Patent
Ina et al.

(10) Patent No.: US 9,540,301 B2
(45) Date of Patent: Jan. 10, 2017

(54) METHOD FOR MANUFACTURING PHOSPHONOCROTONIC ACID DERIVATIVE

(75) Inventors: Shinji Ina, Ageo (JP); Takahiro Yamazaki, Fukuyama (JP); Junichi Sakata, Fukuyama (JP); Koji Ezaki, Kurashiki (JP); Katsuhiro Sakamoto, Fukuyama (JP)

(73) Assignees: KOWA COMPANY, LTD., Nagoya-shi (JP); MANAC Incorporated, Fukuyama-shi (JP)

(*) Notice: Subject to any disclaimer, the term of this patent is extended or adjusted under 35 U.S.C. 154(b) by 333 days.

(21) Appl. No.: 14/113,498

(22) PCT Filed: Apr. 26, 2012

(86) PCT No.: PCT/JP2012/061172
§ 371 (c)(1),
(2), (4) Date: Oct. 23, 2013

(87) PCT Pub. No.: WO2012/147831
PCT Pub. Date: Nov. 1, 2012

(65) Prior Publication Data
US 2014/0051876 A1    Feb. 20, 2014

(30) Foreign Application Priority Data
Apr. 27, 2011    (JP) ................ 2011-099651

(51) Int. Cl.
| | | |
|---|---|---|
| C07C 51/09 | (2006.01) | |
| C07F 9/40 | (2006.01) | |
| C07C 57/03 | (2006.01) | |
| A61K 31/167 | (2006.01) | |
| A61K 31/202 | (2006.01) | |
| A61K 33/16 | (2006.01) | |
| A61K 35/742 | (2015.01) | |
| A61K 35/744 | (2015.01) | |
(Continued)

(52) U.S. Cl.
CPC ............. *C07C 51/09* (2013.01); *A61K 9/4858* (2013.01); *A61K 9/4866* (2013.01); *A61K 9/4875* (2013.01); *A61K 31/167* (2013.01); *A61K 31/202* (2013.01); *A61K 33/16* (2013.01); *A61K 35/742* (2013.01); *A61K 35/744* (2013.01); *A61K 45/06* (2013.01); *C07C 51/353* (2013.01); *C07C 57/03* (2013.01); *C07C 67/343* (2013.01); *C07F 9/4015* (2013.01)

(58) Field of Classification Search
None
See application file for complete search history.

(56) References Cited

U.S. PATENT DOCUMENTS

| | | |
|---|---|---|
| 4,937,308 A | 6/1990 | Knaus et al. |
| 6,369,251 B1 | 4/2002 | Takano et al. |
(Continued)

FOREIGN PATENT DOCUMENTS

| | | |
|---|---|---|
| CA | 2 306 525 A1 | 10/2000 |
| CN | 1099264 A | 3/1995 |
(Continued)

OTHER PUBLICATIONS

Magoulas et al. In European Journal of Medicinal Chemistry 46 (2011) 721-737.*
Rajeshwaran et al. In Organic Letters, 13(6), 1270-1273 (2011).*
Partial Supplementary European Search Report issued Dec. 2, 2014 in Patent Application No. 12776934.7.
P. J. Van Den Tempel, et al., "Vitamin A analogues—V synthesis of 9-, 13-, and 9,13-desmethyl homologues of vitamin A" Tetrahedron, vol. 22, No. 1, XP055152115, Jan. 1, 1966, pp. 293-299.
Alok K. Bhattacharya, et al., "The Michaelis-Arbuzov Rearrangement" Chemical Reviews, vol. 81, No. 4, XP002253799, Jan. 1, 1981, pp. 415-430.
(Continued)

*Primary Examiner* — Dennis Heyer
(74) *Attorney, Agent, or Firm* — Oblon, McClelland, Maier & Neustadt, L.L.P.

(57) ABSTRACT

Provided is a method of manufacturing a high quality phosphonocrotonic acid derivative.
The present invention is a method of manufacturing a compound represented by the following Formula (3) by reacting a compound represented by the following Formula (1) with a compound represented by the following Formula (2), which comprises a treatment process using an acid or base.
[in the formula, $R_1$ represents a $C_{1-6}$ linear or branched alkyl group that may be substituted by a $C_{6-10}$ aryl group, a $C_{2-6}$ linear or branched alkenyl group that may be substituted by a $C_{6-10}$ aryl group, a $C_{2-6}$ linear or branched alkynyl group that may be substituted by a $C_{6-10}$ aryl group, or a $C_{6-10}$ aryl group, $R_2$ represents a hydrogen atom, or a $C_{1-6}$ linear or branched alkyl group that may be substituted by a $C_{6-10}$ aryl group, $R_3$ represents a $C_{1-6}$ linear or branched alkyl group, a $C_{6-10}$ aryl group, or a halogen atom, and X represents a halogen atom, and multiple $R_1$s may be the same or different].

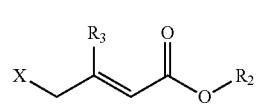

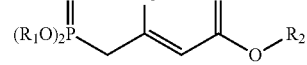

37 Claims, No Drawings

(51) Int. Cl.
*A61K 45/06* (2006.01)
*C07C 67/343* (2006.01)
*C07C 51/353* (2006.01)
*A61K 9/48* (2006.01)

(56) References Cited

U.S. PATENT DOCUMENTS

2004/0242690 A1* 12/2004 Tanikawa .............. C07C 51/09
514/560
2009/0069424 A1   3/2009 Kagawa et al.

FOREIGN PATENT DOCUMENTS

| CN | 1652764 A | 8/2005 |
|----|-----------|--------|
| EP | 0 614 662 A1 | 9/1994 |
| EP | 1 547 588 A1 | 6/2005 |
| JP | 7 118225 | 5/1995 |
| JP | 2001 2621 | 1/2001 |
| JP | 2004 331654 | 11/2004 |
| JP | 2010 189446 | 9/2010 |
| JP | 2012-206950 A | 10/2012 |

OTHER PUBLICATIONS

Ganesan Gobi Rajeshwaran, et al., "Lewis acid-mediated Michaelis-Arbuzov reaction at room temperature: a facile preparation of arylmethyl/heteroarylmethyl phosphonates" Organic Letters, vol. 13, No. 6, XP055152785, Mar. 18, 2011, pp. 1270-1273.

Terry M. Balthazor, et al., "Nickel-catalyzed Arbuzov reaction: mechanistic observations" Journal of Organic Chemistry, vol. 45, No. 26, XP055153329, Dec. 1, 1980, pp. 5425-5426.

Combined Office Action and Search Report issued Jan. 19, 2015 in Chinese Patent Application No. 201280019892.9 (with partial English language translation and English translation of categories of cited documents).

Extended European Search Report issued Feb. 12, 2015 in Patent Application No. 12776934.7.

Combined Taiwanese Office Action and Search Report issued Jul. 15, 2015 in Taiwanese Patent Application No. 101114877 (with English Translation of Categories of Cited Documents).

Magoulas, G .E. et al., "Syntheses, antiproliferative activity and theoretical characterization of acitretin-type retinoids with changes in the lipophilic part", European Journal of Medicinal Chemistry, vol. 46, No. 2, pp. 721-737, (2011).

Duan, Z.-C. et al., "Enantioselective Rh-Catalyzed Hydrogenation of 3-Aryl-4-Phosphonobutenoates with a P-Stereogenic BoPhoz-Type Ligand", Journal of Organic Chemistry, vol. 75, No. 23, pp. 8319-8321 (Sep. 18, 2010).

Iqbal, M. et al., "Synthesis of $^{13}$C single and Double Labelled Retinals, Precursors for NMR Studies of Visual Pigments and Related Systems", Journal of Labelled Compounds and Radiopharmaceuticals , vol. XXII, No. 8, pp. 807-817, (Jan. 4, 1985).

Safaryn, J. E. et al., "A Convenient Synthesis of (±) Ascohlorin", Tetrahedron, vol. 42, No. 10, pp. 2635-2642, (Jan. 13, 1986).

Mata, E. G. et al., "Development of a synthesis of lankacidins: an investigation into 17-membered ring formation", J. Chem. Soc. Perkin Trans. 1, pp. 785-799, (1995).

Ludvik, G. F.et al. ,"The Insecticidal Properties of Some Esters of Phosphorus Acids[1,2,3]", Journal of Economic Entomology, vol. 44, No. 3, pp. 405-418, (Jun. 1951).

International Search Report Issued Aug. 7, 2012 in PCT/JP12/061172 Filed Apr. 26, 2012.

Written Opinion of the International Searching Authority Issued Aug. 7, 2012 in PCT/JP12/061172 Filed Apr. 26, 2012.

Combined Chinese Office Action and Search Report issued Mar. 23, 2016 in Patent Application No. 201280019892.9 (with English language translation and English translation of categories of cited documents).

\* cited by examiner

METHOD FOR MANUFACTURING PHOSPHONOCROTONIC ACID DERIVATIVE

TECHNICAL FIELD

The present invention relates to a method of manufacturing a phosphonocrotonic acid derivative, particularly, triethyl-3-methyl-4-phosphonocrotonate, which is useful as raw materials of a medicine, an agricultural chemical and an industrial product, and a method of manufacturing a useful compound using the same.

BACKGROUND ART

A phosphonocrotonic acid derivative is used in synthesis of various compounds from its high functionality, and particularly, triethyl-3-methyl-4-phosphonocrotonate [ethyl (2E,Z)-4-(diethoxyphosphono)-3-methylbuta-2-enoate, hereinafter, also referred to as "TEMPC"] is useful as a raw material of a medicine, an agricultural chemical and an industrial product, and, for example, is useful in synthesis of a compound having a 3-methylpenta-2,4-dienoate residue (the parts surrounded by the solid lines) represented by the following formulae.

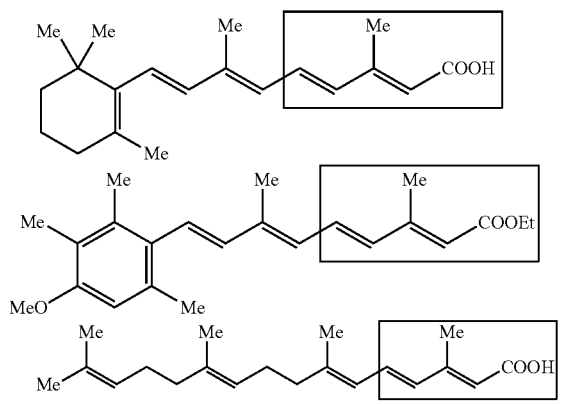

It is known that among them, (2E,4E,6E,8E)-3,7-dimethyl-9-(2,6,6-trimethyl-1-cyclohexene-1-yl)nona-2,4,6,8-tetraenoic acid (generic name: tretinoin) is useful as a therapeutic agent for acute promyelocytic leukemia; and ethyl (2E,4E,6E,8E)-9-(4-methoxy-2,3,6-trimethylphenyl)-3,7-dimethylnona-2,4,6,8-tetraenoate (generic name: etretinate) is useful as a therapeutic agent for a family of psoriasis, a family of ichthyosis, and the like; and (2E,4E,6E,10E)-3,7,11,15-tetramethylhexadeca-2,4,6,10,14-pentaenoic acid (generic name: peretinoin) is useful as an inhibitor for liver cell cancer recurrence. TEMPC can be an important raw material for manufacture of these compounds (Patent Document 1).

It is known that TEMPC can be manufactured by Arbuzov reaction in which ethyl 4-bromo-3-methylcrotonate is reacted with triethyl phosphite as illustrated in Scheme 1 described below.

(scheme 1)

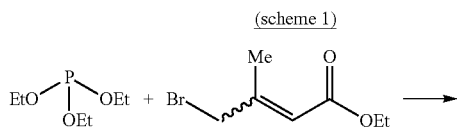

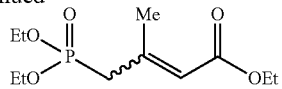

With respect to the reaction, specifically, for example, a method in which a mixture of a cis form and a trans form of ethyl 4-bromo-3-methylcrotonate is reacted with triethyl phosphite at 90° C. for 3 hours, and then distillation is performed to obtain TEMPC as a mixture of a cis/trans form=40/60 (Non-Patent Document 1); a method in which the trans form of ethyl 4-bromo-3-methylcrotonate is reacted with triethyl phosphite at 120° C. for 30 minutes, and then distillation is performed to remove bromoethane, and the reaction mixture is further reacted for 2 hours, and then distillation is performed, whereby a trans form of TEMPC (Non-Patent Document 2) can be obtained; or a method in which a trans form of ethyl 4-bromo-3-methylcrotonate is reacted with triethyl phosphite at 165 to 175° C. for 5 minutes, and then distillation is performed to obtain a trans form of TEMPC (Non-Patent Document 3).

CITATION LIST

Patent Document

Patent Document 1: Japanese Patent Application Laid-Open (JP-A) No. 2004-331654

Non-Patent Document

Non-Patent Document 1: Journal of Labelled Compounds and Radiopharmaceuticals, 22, 807-17; 1985
Non-Patent Document 2: Tetrahedron, 42, 2635-42; 1986
Non-Patent Document 3: J. Chem. Soc. Perkin Trans 1, 1995, 785-99
Non-Patent Document 4: J. Econ. Entomol., 44, 405-418; 1951

SUMMARY OF INVENTION

Technical Problem

The present inventors found out for the first time that when TEMPC is manufactured with the methods described in Non-Patent Documents 1 to 3, tetraethyl pyrophosphate (hereinafter, also referred to as "TEPP") represented by the following formula is by-produced.

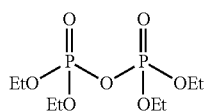

A pyrophosphoric acid ester such as TEPP has strong neurotoxicity such as choline esterase inhibitory action and the like, and also has insecticidal action (Non-Patent Document 4), and thus TEPP is conventionally used as an organic phosphorous agricultural chemical. Consequently, removal or lowering of TEPP not only improves the quality of TEMPC and a compound synthesized using this as a raw material, but also is important in an aspect of securing the safety of a manufacture worker, and the like. However, Non-Patent Documents 1 to 3 did not describe or suggest the presence of TEPP, and the present inventors also did not expect production of TEPP. Furthermore, TEPP was not removable or lowerable with the method described in Patent Document 1.

Consequently, an object of the present invention is to provide a method of manufacturing a high quality phosphonocrotonic acid derivative. More specifically, an object of the present invention is to provide a method of manufacturing a phosphonocrotonic acid derivative with lowered content of pyrophosphoric acid ester, preferably to provide a method of manufacturing TEMPC with lowered content of TEPP.

Solution to Problem

The present inventors performed earnest investigation to resolve the above-mentioned subject, as a result, found out that a phosphonocrotonic acid derivative with lowered content of pyrophosphoric acid ester, which is an impurity, is obtained by treatment with use of an acid or base in manufacturing of the phosphonocrotonic acid derivative from a halocrotonic acid ester and a phosphite ester. The present inventors performed the investigation further specifically, and found out that it is possible to manufacture a compound having a 3-methylpenta-2,4-dienoic acid residue that is substantially free of pyrophosphoric acid ester by reacting the phosphonocrotonic acid derivative manufactured by the present method as a raw material with a carbonyl compound, and thus completed the present invention.

That is to say, the present invention provides those described below.

[1] A method of manufacturing a compound represented by Formula (3) described below by reacting a compound represented by Formula (1) described below with a compound represented by Formula (2) described below, the method comprising a treatment process using an acid or base.

(in the formula, $R_1$ represents a $C_{1-6}$ linear or branched alkyl group that may be substituted by a $C_{6-10}$ aryl group; a $C_{2-6}$ linear or branched alkenyl group that may be substituted by a $C_{6-10}$ aryl group; a $C_{2-6}$ linear or branched alkynyl group that may be substituted by a $C_{6-10}$ aryl group; or a $C_{6-10}$ aryl group, and each $R_1$ may be the same or different)

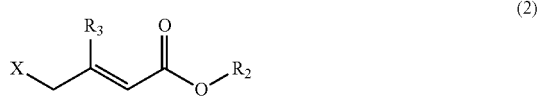

(in the formula, X represents a halogen atom, $R_2$ represents a hydrogen atom, or a $C_{1-6}$ linear or branched alkyl group that may be substituted by a $C_{6-10}$ aryl group, and $R_3$ represents a $C_{1-6}$ linear or branched alkyl group, a $C_{6-10}$ aryl group, or a halogen atom.)

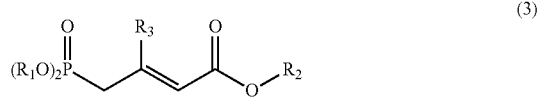

(in the formula, $R_1$, $R_2$ and $R_3$ are the same as described above, and each $R_1$ may be the same or different.)

[2] A method of manufacturing a compound having a 3-methylpenta-2,4-dienoic acid residue, the method comprising reacting a compound represented by Formula (3) obtained by the above-mentioned manufacturing method with a carbonyl compound.

[3] A method of manufacturing a compound having a 3-methylpenta-2,4-dienoic acid residue by performing a treatment using an acid or base at the time of the reaction between a compound represented by Formula (1) with a compound represented by Formula (2), or after the reaction, whereby a compound represented by Formula (3) is obtained, and then reacting the compound with a carbonyl compound.

[4] (2E,4E,6E,10E)-3,7,11,15-tetramethylhexadeca-2,4,6,10,14-pentaenoic acid that is substantially free of tetraethyl pyrophosphate.

[5] A pharmaceutical composition comprising (2E,4E,6E,10E)-3,7,11,15-tetramethylhexadeca-2,4,6,10,14-pentaenoic acid described in the above-mentioned [4].

Effect of the Invention

According to the method of the present invention, it is possible to manufacture a phosphonocrotonic acid derivative in higher purity, and for example, it is possible to manufacture TEMPC with lowered content of TEPP. In addition, according to the method of the present invention, it is possible to manufacture a medicine, an agricultural chemical and an industrial product with high quality by using a phosphonocrotonic acid derivative with lowered content of pyrophosphoric acid ester as a raw material, and specifically for example, it is possible to manufacture (2E,4E,6E,8E)-3,7-dimethyl-9-(2,6,6-trimethyl-1-cyclohexene-1-yl)nona-2,4,6,8-tetraenoic acid, ethyl (2E,4E,6E,8E)-9-(4-methoxy-2,3,6-trimethylphenyl)-3,7-dimethylnona-2,4,6,8-tetraenoate, or (2E,4E,6E,10E)-3,7,11,15-tetramethylhexadeca-2,4,6,10,14-pentaenoic acid that is substantially free of pyrophosphoric acid ester such as TEPP.

DESCRIPTION OF EMBODIMENTS

Definitions of the terms as used herein are as described below.

The "halogen atom" as used herein means a fluorine atom, a chlorine atom, a bromine atom, or an iodine atom. The "halogen atom" is preferably a fluorine atom, a chlorine atom or a bromine atom, and more preferably a bromine atom.

The "linear or branched alkyl group" as used herein is a monovalent group in which one hydrogen atom is removed from an aliphatic saturated hydrocarbon, and encompasses linear and branched groups. Examples of the $C_{1-6}$ linear or branched alkyl group include specifically, for example, a methyl group, an ethyl group, an n-propyl group, an isopropyl group, an n-butyl group, an isobutyl group, a s-butyl group, a t-butyl group, a n-pentyl group, an isopentyl group, a 2-methylbutyl group, a neopentyl group, a 1-ethylpropyl group, an n-hexyl group, an isohexyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group, a 1,2-dimethylbutyl group, a 1,3-dimethylbutyl group, a 2,3-dimethylbutyl group, a 1-ethylbutyl group, a 2-ethylbutyl group and the like. Among these, the $C_{1-6}$ linear or branched alkyl group is preferably a methyl group, an ethyl group, an isopropyl group or a neopentyl group, and more preferably an ethyl group or an isopropyl group.

The "linear or branched alkenyl group" as used herein means a linear or branched alkenyl group having a carbon-carbon double bond at any one or more sites on the alkyl chain. Examples of the $C_{2-6}$ linear or branched alkenyl group include specifically, for example, an ethenyl group (a vinyl group), a propa-1-en-1-yl group, a propa-2-en-1-yl group, a propa-1-en-2-yl group, a buta-1-en-1-yl group, a buta-2-en-1-yl group, a buta-3-en-1-yl group, a buta-1-en-2-yl group, a buta-3-en-2-yl group, a penta-1-en-1-yl group, a penta-2-en-1-yl group, a penta-3-en-1-yl group, a penta-4-en-1-yl group, a penta-1-en-2-yl group, a penta-4-en-2-yl group, a 3-methylbuta-1-en-1-yl group, a 3-methylbuta-2-en-1-yl group, a 3-methylbuta-3-en-1-yl group, a hex-1-en-1-yl group, a hex-5-en-1-yl group, a 4-methylpenta-3-en-1-yl group and the like, and preferably an ethenyl group, a propa-2-en-1-yl group, a buta-2-en-1-yl group, and a 3-methylbuta-3-en-1-yl group.

The "linear or branched alkynyl group" as used herein means a linear or branched alkynyl group having a carbon-carbon triple bond at any one or more sites on the alkyl chain. Examples of the $C_{2-6}$ linear or branched alkynyl group include specifically, for example, an ethynyl group, a propa-1-yne-1-yl group, a propa-2-yne-1-yl group, a buta-1-yne-1-yl group, a buta-3-yne-1-yl group, a 1-methylpropa-2-yne-1-yl group, a penta-1-yne-1-yl group, a penta-4-yne-1-yl group, a hex-1-yne-1-yl group, a hex-5-yne-1-yl group and the like, and preferably a propa-2-yne-1-yl group.

The "aryl group" as used herein means an aromatic hydrocarbon group. Examples of the $C_{6-10}$ aryl group include specifically, for example, a phenyl group, a naphthyl group or an azulenyl group, and preferably a phenyl group. With respect to other groups that are not defined herein, the other groups follow ordinary definitions.

The "substantially free of pyrophosphoric acid ester" as used herein refers that the residual ratio of the pyrophosphoric acid ester in the analysis conditions described in Examples described later is less than 5%, and preferably less than 4%. This is similar with respect to "TEPP".

Hereinafter, the manufacturing method of the present invention will be described.

The manufacturing method of the present invention may be illustrated in Scheme 2 described below.

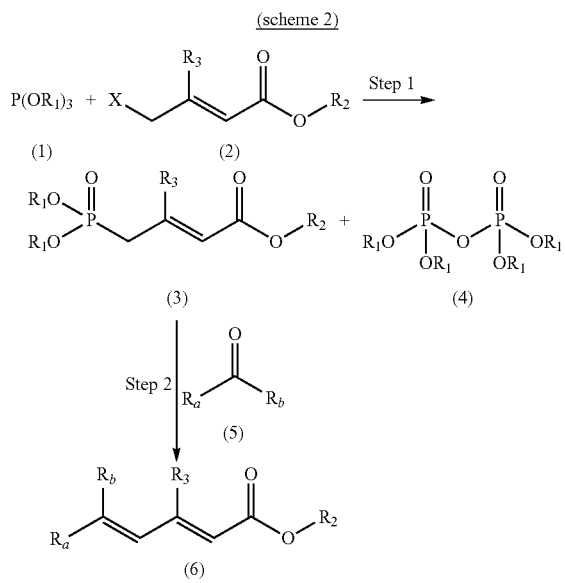

(In Scheme 2, $R_a$ and $R_b$ each independently represent a hydrogen atom or an organic group, $R_1$, $R_2$, $R_3$ and X are the same as described above, and multiple $R_1$s may be the same or different, with the proviso that $R_a$ and $R_b$ are not a hydrogen atom at the same time.)

Examples of the organic group in $R_a$ and $R_b$ may include hydrocarbon groups. Examples of the hydrocarbon group include an aliphatic hydrocarbon group, an alicyclic hydrocarbon group, an aryl group and the like, which may have a substituent. Examples of the substituent include a halogen atom, a hydroxyl group, a $C_{1-6}$ alkoxy group, a phenyl group, an alicyclic hydrocarbon group and the like, and the phenyl group and the alicyclic hydrocarbon group may be substituted by a halogen atom, a hydroxyl group, a $C_{1-6}$ alkyl group or a $C_{1-6}$ alkoxy group. Meanwhile, the position and the number of the substituent are arbitrary, and in the case where the hydrocarbon group has 2 or more substituents, the substituents may be the same or different.

Examples of the $C_{1-6}$ alkoxy group include for example, a methoxy group, an ethoxy group, a propoxy group, an isopropoxy group, a butoxy group and the like. Among these, the $C_{1-6}$ alkoxy group is preferably a methoxy group or an ethoxy group. In addition, the $C_{1-6}$ alkyl group may be linear or branched chain, and specific examples thereof may include those described above.

Examples of the aliphatic hydrocarbon group include an alkyl group, an alkenyl group and an alkynyl group. The carbon number of these aliphatic hydrocarbon groups is preferably 1 to 32, more preferably 1 to 30, and further preferably 1 to 20. In addition, these aliphatic hydrocarbon groups may be linear or branched.

The alkyl group is preferably a $C_{1-30}$, more preferably a $C_{1-25}$, and even more preferably a $C_{1-20}$ alkyl group, and specifically examples thereof may include a decyl group, a undecyl group, a 1-methyldecyl group, a pentadecyl group, an octadecyl group and the like in addition to the specific examples as described above.

In addition, the alkenyl group is preferably a $C_{2-32}$, more preferably a $C_{5-30}$ alkenyl group, and specifically, examples thereof may include an octa-2-en-1-yl group, a deca-2-en-1-yl group, a 2-methylbuta-1,3-dienyl group, a 6-methyleneocta-2,7-dien-2-yl group, a 6-methylocta-2,5,7-trien-2-yl group, 6,10,15,19,23-pentamethyltetracosa-2,6,10,14,18,22-hexaen-2-yl, a 2,6,10-trimethylundeca-1,5,9-trienyl group and the like in addition to the specific examples as described above. The alkenyl group may be substituted with an aryl group, or an alicyclic hydrocarbon group described later, and for example, examples of the aryl-substituted alkenyl group may include a 4-(4-methoxy-2,3,6-trimethylphenyl)-2-methylbuta-1,3-dienyl group and the like, and examples of the alicyclic hydrocarbon-substituted alkenyl group may include a 4-(2,6,6-trimethyl-1-cyclohexenyl)-2-methylbuta-1,3-dienyl group and the like, respectively.

Furthermore, the alkynyl group is preferably a $C_{2-30}$, more preferably a $C_{2-25}$, and even more preferably a $C_{2-20}$ alkynyl group, and specifically, examples of the alkynyl group may include an octa-2-yne-1-yl group, a deca-2-yne-1-yl group and the like in addition to the specific examples as described above.

Examples of the alicyclic hydrocarbon group may include a cycloalkyl group, a cycloalkenyl group, a condensed polycyclic hydrocarbon group, a bridged cyclic hydrocarbon group, a cyclic terpene hydrocarbon group and the like. The carbon number of these alicyclic hydrocarbon groups is preferably 3 to 30, more preferably 3 to 25, and even more preferably 3 to 20. Specific examples of the cycloalkyl group include a cyclopropyl group, a cyclobutyl group, a cyclohexyl group, a t-butylcyclohexyl group, a cyclooctyl group and the like. In addition, specific examples of the cycloalkenyl group include a 1-cyclohexenyl group and the like. Specific examples of the condensed polycyclic hydrocarbon group include a tricyclodecanyl group, an adamantyl group and the like. Examples of the bridged cyclic hydrocarbon group include a pentacyclopentadecanyl group, an isobornyl group, tricyclopentenyl group and the like. Examples of the cyclic terpene hydrocarbon group may include a monovalent group and the like in which one hydrogen atom is removed from m-menthane, m-menthene, thujane, carane, pinane, bornane, norcarane, norpinane, norbornane and the like.

The aryl group is preferably a $C_{6-20}$, and even more preferably a $C_{6-10}$ aryl group. Specific examples of the aryl group may include those described above.

Among them, $R_a$ is preferably a substituted or unsubstituted aliphatic hydrocarbon group, and more preferably a substituted or unsubstituted alkenyl group. In addition, $R_b$ is preferably a hydrogen atom or a substituted or unsubstituted aliphatic hydrocarbon group, and more preferably a hydrogen atom.

Hereinafter, each step will be described.

In Scheme 2, the step 1 is a process of reacting a compound represented by Formula (1) (hereinafter, also referred to as "compound (1)") with a compound represented by Formula (2) (hereinafter, also referred to as "compound (2)"), to obtain a compound represented by Formula (3) (a phosphonocrotonic acid derivative) by $S_N 2$ reaction of the compound (1) to the compound (2).

This reaction can be performed according to the conditions of conventionally well-known Arbuzov reaction. For example, the conditions described in Russ. Phys. Chem. Soc. 1906, 38, 687, or Russ. Phys. Chem. Soc. 1910, 42, 395 and the like may be applied, but the conditions are not limited thereto.

The compound (1) used in the step 1 can be obtained, for example, by reaction between phosphorus trichloride and an alcohol. In addition, the compound (2) can be obtained, for example, by halogenating a crotonic acid ester compound with a halogenating agent such as N-halosuccinic imide. The compound (1) and the compound (2) may use a commercialized product. The alcohol is preferably a $C_{1-6}$ alcohol, and examples of the alcohol may include, for example, methanol, ethanol, propanol, isopropanol and the like. Among these, the alcohol is preferably methanol or ethanol.

The present invention is characterized by including a treatment process using an acid or base in manufacture of the phosphonocrotonic acid derivative by reacting the compound (1) with the compound (2).

The treatment process is specifically preferably either one or both of (A) and (B) described below.

(A) Process of reacting the compound (1) with the compound (2) in the presence of an acid or base.

(B) Process of reacting the compound (1) with the compound (2), and then performing a treatment using an acid or base.

By this, it is possible to lower the content of a compound represented by Formula (4) (pyrophosphoric acid ester) wherein TEPP is typical of the pyrophosphoric acid ester.

A method for the treatment process is not particularly limited if at least contact treatment is performed using an acid or base at the time of the reaction of the compound (1) with the compound (2), or after the reaction. For example, in the case of the process (A), the acid or base may be added to the reaction system, and in the case of the process (B), the acid or base may be added and contacted, for example, to a reaction solution after the reaction, to a solution of the organic layer separated after the reaction, or to a solution in which the phosphonocrotonic acid derivative isolated with distillation and the like is dissolved again in an organic solvent, and the like. The contact treatment may be performed once, twice or more times. Meanwhile, examples of the organic solvent may include, for example, hydrocarbons (for example, heptane, hexane, toluene, benzene, xylene), and halogenation hydrocarbons (for example, dichloromethane, chloroform, chlorobenzene), which may be used in one kind or in combination of two or more kinds.

As the acid used in the treatment process of the present invention, any one of organic acid and inorganic acid may be used, which may be used in one kind or in combination of two or more kinds. Examples of the inorganic acid include, for example, hydrochloric acid (pKa=−7), sulfuric acid (pKa=−3), nitric acid (pKa=−1.4), phosphoric acid (pKa=2.12), nitrous acid (3.15) and the like. Examples of the organic acid include, for example, trifluoroacetic acid (pKa=0.3), oxalic acid (pKa=1.27), formic acid (pKa=3.54), acetylacetic acid (pKa=3.57), lactic acid (pKa=3.64), succinic acid (pKa=3.99), benzoic acid (pKa=4.00), adipic acid (pKa=4.26), acetic acid (pKa=4.76), propionic acid (pKa=4.87) and the like.

The acid used in the treatment process is preferably an acid having less than 5 of pKa, more preferably an acid having −5 or more and less than 5 of pKa, and further preferably an acid having −5 or more and less than 3 of pKa. Among them, the acid used in the treatment process is preferably sulfuric acid, nitric acid, phosphoric acid, acetic acid or trifluoroacetic acid, oxalic acid, and further preferably sulfuric acid. Herein, the "pKa" in the specification refers to the acid dissociation constant at 25° C., which is the dissociation constant of the first acid in the case of a multivalent acid. Meanwhile, the pKa value of an acid may refer to the numerical value described in a document and the like.

As the acid in the present invention, a solid acid may be used, and examples thereof include, for example, an acid type ion exchange resin, an activated clay, a silica-alumina and the like. As the acid type ion exchange resin, a commercialized product such as Dowex (manufactured by The Dow Chemical Company), Nafion (manufactured by Du Pont) and DIAION (manufactured by Mitsubishi Chemical Corporation) may be used.

In addition, the acid may be used as a solution including an aqueous solution. The concentration of the solution in the case where the acid is used as a solution is such that the upper limit is preferably less than 100 mass %, more preferably less than 90 mass %, and further preferably less than 60 mass %, whereas the lower limit is preferably 1 mass %, more preferably 3 mass %, and is further preferably 5 mass %. The concentration range of the acid solution is preferably 1 mass % or more and less than 100 mass %, more preferably 3 mass % or more and less than 90 mass %, and further preferably 5 mass % or more and less than 60 mass %. The pH (25° C.) of the aqueous solution of the acid used in the treatment process of the present invention is not particularly limited, but is preferably pH 1 to 5, and more preferably pH 1 to 3.

As the base used in the treatment process of the present invention, any one of an inorganic base, an organic base, a metal alkoxide and an alkyl metal may be used, which may be used in one kind or in combination of two or more kinds.

The inorganic base is not particularly limited, but for example, ammonia (pKb=4.64), and an alkali metal hydroxide, an alkali metal hydride, an alkali metal carbonate, an alkali metal hydrogen carbonate, an alkali metal hydrogen phosphate, or an alkali metal may be used. The alkali metal hydroxide is preferably, for example, lithium hydroxide, sodium hydroxide, potassium hydroxide and the like. The alkali metal hydride is preferably, for example, lithium hydride, sodium hydride (pKb=0.2), potassium hydride and the like. The alkali metal carbonate is preferably, for example, lithium carbonate, sodium carbonate (pKb=3.67), potassium carbonate, cesium carbonate and the like. The alkali metal hydrogen carbonate is preferably, for example, sodium hydrogen carbonate (pKb=3.67), potassium hydrogen carbonate, cesium hydrogen carbonate and the like. The alkali metal hydrogen phosphate is preferably, for example, disodium hydrogen phosphate, disodium hydrogen phosphate (pKb=1.60), dipotassium hydrogen phosphate, potassium dihydrogen phosphate and the like. The alkali metal is preferably, for example, metal lithium, metal sodium, metal potassium and the like.

Examples of the organic base include is not particularly limited, but for example, a nitrogen-containing heterocyclic compound or an organic amine may be used. The nitrogen-containing heterocyclic compound is preferably, for example, pyridine (pKb=8.33), 4-dimethylaminopyridine (DMAP) (pKb=4.80), lutidine (pKb=7.04), collidine and the like, and the organic amine is preferably, for example, trimethylamine (pKb=4.24), dimethylamine (pKb=2.98), triethylamine (pKb=3.32), diethylamine (pKb=2.98), N,N-diisopropylethylamine, N,N-diisopropylpentylamine, morpholine (pKb=5.64), piperidine (pKb=2.76), pyrrolidine (pKb=2.6), 1,8-diazabicyclo[5.4.0]undeca-7-ene (DBU) (pKb=2.00), 1,5-diazabicyclo[4.3.0]nona-5-ene (DBN), 1,4-diazabicyclo[2.2.2]octane (DABCO) and the like.

The metal alkoxide is not particularly limited, but is preferably, for example, sodium methoxide, potassium methoxide, sodium ethoxide, potassium ethoxide, t-butoxy sodium, t-butoxy potassium and the like.

The alkyl metal is not particularly limited, but is preferably, for example, lithium diisopropylamide, sodium diisopropylamide, potassium diisopropylamide, lithium hexamethyl disilazide, sodium hexamethyl disilazide, potassium hexamethyl disilazide, n-butyl lithium, s-butyl lithium, t-butyl lithium and the like.

The base used in the treatment process is preferably those having a pKb of 0 to 6, and more preferably those having a pKb of 2 to 5. Specifically, the base is preferably sodium hydroxide, sodium carbonate, sodium hydrogen carbonate, triethylamine, 4-dimethylaminopyridine or sodium methoxide, and more preferably sodium hydroxide. Herein, the "pKb" in the specification refers to the dissociation constant of the base at 25° C., and the dissociation constant of the first acid in the case of a multivalent base. Meanwhile, the pKb value of a base may refer to the numerical value described in a document and the like.

In addition, the base may be used as a solution including an aqueous solution. The concentration of the base solution in the case where the base is used as a solution is such that the upper limit is preferably less than 100 mass %, more preferably less than 80 mass %, even more preferably less than 50 mass %, even more preferably less than 30 mass %, and further preferably 10 mass %, whereas the lower limit is preferably 1 mass %. The concentration range of the base solution is preferably 1 mass % or more and less than 50 mass %, more preferably 1 mass % or more and less than 30 mass % and further preferably 1 to 10 mass %. The pH (25° C.) of the aqueous solution of the base used in the treatment process of the present invention is not particularly limited, but is preferably pH 8 to 14, and more preferably pH 11 to 12.

The addition amount of the acid or base used in the treatment process of the present invention is not particularly limited, but for example, is preferably 1 to 50 mass %, and further preferably 5 to 20 mass % with respect to a reaction solution after the reaction, a solution of the organic layer after the reaction, and a solution obtained by re-dissolution in an organic solvent after the isolation in the case of the process (B). The same addition amount as described above may be also adopted in the case of the process (A).

The temperature in the treatment process of the present invention is not particularly limited, but is preferably 0 to 100° C., more preferably 1 to 90° C., even more preferably 20 to 80° C., and further preferably 40 to 70° C. The time in the treatment process of the present invention is not particularly limited, but preferably is 1 to 15 hours, more preferably 3 to 15 hours, even more preferably 3 to 10 hours, and further preferably 3 to 5 hours.

The treatment process of the present invention may be performed further in the presence of an alcohol. The alcohol is preferably added since the organic layer and the aqueous layer become uniform with the addition. The alcohol that can be used is not particularly limited, but is preferably methanol, ethanol, 1-propanol, 2-propanol and the like, and further preferably methanol or ethanol.

The amount of the alcohol used is not particularly limited, but is preferably 1 to 50 mass %, more preferably 5 to 20 mass %, and further preferably 8 to 15 mass % with respect to a reaction solution after the reaction, a solution of the organic layer after the reaction, or a solution obtained by re-dissolution in an organic solvent after the isolation.

By subjecting to a general purification means such as centrifugation, separation, washing, concentration, drying, distillation and column chromatography as necessary after the treatment process, it is possible to isolate a phosphonocrotonic acid derivative with removed or lowered pyrophosphoric acid esters including TEPP that are impurities.

Hereinafter, the step 2 will be described.

In Scheme 2, the step 2 is a process of reacting the phosphonocrotonic acid derivative with a compound represented by Formula (5) (carbonyl compound), whereby to obtain a compound represented by Formula (6) (a compound having a 3-methylpenta-2,4-dienoic acid residue) by the Horner-Emmons reaction of the phosphonocrotonic acid derivative and the carbonyl compound. Meanwhile, the compound represented by Formula (5) is not particularly limited if it is a carbonyl compound allowing Horner-Emmons reaction, but examples thereof may include, for example, farnesal, β-ionylidene acetaldehyde, (2E,4E)-5-(4-methoxy-2,3,6-trimethylphenyl)-3-methylpenta-2,4-dienal and the like.

This reaction can be performed according to conventionally well-known conditions of Horner-Emmons reaction. For example, the conditions described in Chemical Reviews 1974, 74, 87-99 and the like may be applied, but the conditions are not limited thereto. In addition, in the case where the compound represented by Formula (6) produced by Horner-Emmons reaction of the phosphonocrotonic acid derivative and the carbonyl compound is an ester compound, hydrolysis thereof can give a compound having a 3-methylpenta-2,4-dienoic acid residue in which the ester group is converted to a carboxyl group. Meanwhile, for the hydrolysis, conventionally well-known method may be applied. Then, the compound having a 3-methylpenta-2,4-dienoic acid residue may be isolated and purified by centrifugation, separation, washing, concentration, drying, recrystallization, distillation, column chromatography, or a combination thereof.

The phosphonocrotonic acid derivative used in the step 2 is substantially free of pyrophosphoric acid ester, and thus it is possible in the present invention to obtain a compound having a 3-methylpenta-2,4-dienoic acid residue in high purity. For example, it is possible to obtain (2E,4E,6E,10E)-3,7,11,15-tetramethylhexadeca-2,4,6,10,14-pentaenoic acid in high purity by using TEMPC obtained in the step 1 as the phosphonocrotonic acid derivative, and farnesal as the carbonyl compound, respectively as raw material compounds. In addition, it is possible to obtain (2E,4E,6E,8E)-3,7-dimethyl-9-(2,6,6-trimethyl-1-cyclohexene-1-yl)nona-2,4,6,8-tetraenoic acid in high purity by using TEMPC obtained in the step 1 as the phosphonocrotonic acid derivative and β-ionylidene acetaldehyde as the carbonyl compound, respectively as the raw material compounds. Furthermore, it is possible to obtain ethyl (2E,4E,6E,8E)-9-(4-methoxy2,3,6-trimethylphenyl)-3,7-dimethylnona-2,4,6,8-tetraenoate in high purity by using TEMPC obtained in the step 1 as the phosphonocrotonic acid derivative and (2E,4E)-5-(4-methoxy-2,3,6-trimethylphenyl)-3-methylpenta-2,4-dienal as the carbonyl compound, respectively as the raw material compounds.

Thus-obtained compound having a 3-methylpenta-2,4-dienoic acid residue is of high purity that is substantially free of pyrophosphoric acid ester, that is an impurity, and thus is with excellent quality.

Consequently, a compound having a 3-methylpenta-2,4-dienoic acid residue that is substantially free of pyrophosphoric acid ester, particularly preferably (2E,4E,6E,10E)-3,7,11,15-tetramethylhexadeca-2,4,6,10,14-pentaenoic acid, (2E,4E,6E,8E)-3,7-dimethyl-9-(2,6,6-trimethyl-1-cyclohexene-1-yl)nona-2,4,6,8-tetraenoic acid, or ethyl (2E,4E,6E,8E)-9-(4-methoxy-2,3,6-trimethylphenyl)-3,7-dimethylnona-2,4,6,8-tetraenoate that is substantially free of TEPP, is useful as raw materials of a pharmaceutical composition. The pharmaceutical composition is substantially free of pyrophosphoric acid ester that is an impurity, and thus is with excellent quality.

The pharmaceutical composition of the present invention can be made to various dosage forms by using formulation additives suitably in accordance with a well-known method described in GENERAL RULES FOR PREPARATIONS, The Japanese Pharmacopeia 16$^{th}$ edition and the like. Examples of the formulation in the present invention include various formulations such as preparations for oral administration, preparations for oro-mucosal application, and preparations for injection. The dosage form is not particularly limited, but examples thereof include, for example, a tablet (including orally disintegrating tablet, a chewable tablet, a dispersible tablet, soluble tablet; tablets for oro-mucosal applications such as a lozenge, a sublingual tablet, a buccal tablet, mucoadhesive tablet and a medicated chewing gum), a capsule, a pill, a powder, a granule, a subtle granule, a dry syrup, an oral jelly, an oral solution (an elixir, a suspension, an emulsion, a lemonade and the like), a syrup and the like.

The dosage of the pharmaceutical composition of the present invention may be suitably selected depending on the kind of the disease to be applied, the purpose of the prevention or treatment, conditions of the patient such as the age, the weight and the symptom, but the dosage for an adult per a day is, for example, 10 to 1000 mg or so, as the amount of the active ingredient in the oral administration. The above-mentioned dosage may be generally administered in one to several divisions per a day, but also may be administered every several days.

For example, in the case where tretinoin obtained by the present invention is used, 60 to 80 mg per a day is preferably orally administered in three divisions. In addition, in the case where etretinate is used, 10 to 75 mg per a day is preferably orally administered in one to three divisions. In case of using peretinoin, 200 to 1000 mg per a day is preferably orally administered in one to three divisions.

In relation to the embodiments described above, the present invention further discloses the manufacturing method, the compound, and the pharmaceutical composition described below.

<1> A method of manufacturing a compound represented by Formula (3) described below by reacting a compound represented by the following Formula (1) and a compound represented by the following Formula (2), wherein the method comprises a treatment process using an acid or base.

$(R_1O)_3P$            (1)

wherein $R_1$ represents a $C_{1-6}$ linear or branched alkyl group that may be substituted by a $C_{6-10}$ aryl group, a $C_{2-6}$ linear or branched alkenyl group that may be substituted by a $C_{6-10}$ aryl group, a $C_{2-6}$ linear or branched alkynyl group that may be substituted by a $C_{6-10}$ aryl group, or a $C_{6-10}$ aryl group, and each $R_1$ may be the same or different.

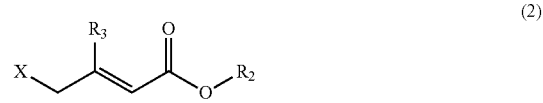

wherein X represents a halogen atom, $R_2$ represents a hydrogen atom, or a $C_{1-6}$ linear or branched alkyl group that may be substituted by a $C_{6-10}$ aryl group, and R3 represents a $C_{1-6}$ linear or branched alkyl group, a $C_{6-10}$ aryl group, or a halogen atom.

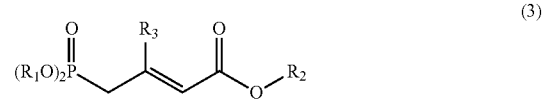

wherein $R_1$, $R_2$, and $R_3$ are as described above, and each $R_1$ may be the same or different.

<2> The method as described in the above-mentioned <1> wherein the treatment process comprises either one or both of (A) and (B) described below.

(A) Process of reacting the compound represented by Formula (1) with the compound represented by Formula (2) in the presence of an acid or base.

(B) Process of reacting the compound represented by Formula (1) with the compound represented by Formula (2), and then treating with an acid or base.

<3> The method as described in above-mentioned <1> or <2>, wherein triethyl phosphite as the compound represented by Formula (1), and ethyl 4-bromo-3-methylcrotonate as the compound represented by Formula (2) are used, respectively, to manufacture triethyl-3-methyl-4-phosphonocrotonate as a compound represented by Formula (3).

<4> A method of manufacturing a compound having a 3-methylpenta-2,4-dienoic acid residue by reacting a compound represented by Formula (3) obtained by the method as described in any one of the above-mentioned <1> to <3> with a carbonyl compound.

<5> The method as described in the above-mentioned <4>, wherein triethyl-3-methyl-4-phosphonocrotonate as the compound represented by Formula (3) and farnesal as the carbonyl compound are used, respectively, to manufacture (2E,4E,6E,10E)-3,7,11,15-tetramethylhexadeca-2,4,6,10,14-pentaenoic acid as a compound having a 3-methylpenta-2,4-dienoic acid residue.

<6> The method as described in the above-mentioned <4>, wherein triethyl-3-methyl-4-phosphonocrotonate as the compound represented by Formula (3) and β-ionylidene acetaldehyde as the carbonyl compound are used, respectively, to manufacture (2E,4E,6E,8E)-3,7-dimethyl-9-(2,6,6-trimethyl-1-cyclohexene-1-yl)nona-2,4,6,8-tetraenoic acid as the compound having a 3-methylpenta-2,4-dienoic acid residue.

<7> The method as described in the above-mentioned <4>, wherein triethyl-3-methyl-4-phosphonocrotonate as the compound represented by Formula (3) and (2E,4E)-5-(4-methoxy-2,3,6-trimethylphenyl)-3-methylpenta-2,4-dienal as the carbonyl compound are used, respectively, to manufacture ethyl (2E,4E,6E,8E)-9-(4-methoxy-2,3,6-trimethylphenyl)-3,7-dimethylnona-2,4,6,8-tetraenoate as the compound having a 3-methylpenta-2,4-dienoic acid residue.

<8> A method of manufacturing a compound having a 3-methylpenta-2,4-dienoic acid residue by performing a treatment using an acid or base at the time of the reaction of a compound represented by Formula (1) with a compound represented by Formula (2), or after the reaction, whereby a compound represented by Formula (3) is obtained, and then reacting the compound with a carbonyl compound.

<9> The method as described in any one of the above-mentioned <1> to <8>, wherein the acid is an acid having a pKa of preferably less than 5, more preferably −5 or more and less than 5, and further preferably −5 or more and less than 3.

<10> The method as described in any one of the above-mentioned <1> to <9>, wherein the acid is used as a solution, and the concentration of the acid solution is preferably less than 100 mass %, more preferably than 90 mass % less, and further preferably less than 60 mass %, and preferably 1 mass % or more, more preferably 3 mass % or more, and further preferably 5 mass % or more.

<11> The method as described in any one of the above-mentioned <1> to <10>, wherein an aqueous solution of the acid has the pH of preferably 1 to 5, and more preferably 1 to 3.

<12> The method as described in any one of the above-mentioned <1> to <11>, wherein the acid is an inorganic acid.

<13> The method as described in the above-mentioned <12>, wherein the inorganic acid is sulfuric acid or phosphoric acid.

<14> The method as described in any one of the above-mentioned <1> to <11>, wherein the acid is an organic acid.

<15> The method as described in the above-mentioned <14>, wherein the organic acid is acetic acid.

<16> The method as described in any one of the above-mentioned <1> to <8>, wherein the base is a base having a pKb of preferably 0 to 6, and more preferably 2 to 5.

<17> The method as described in any one of the above-mentioned <1> to <8> and <16>, wherein the base is used as a solution, and the concentration of the base solution is preferably less than 100 mass %, more preferably less than 80 mass %, even more preferably less than 50 mass %, even more preferably less than 30 mass %, and further preferably equal to or less than 10 mass %, and preferably 1 mass % or more.

<18> The method as described in any one of the above-mentioned <1> to <8> and <16> and <17>, wherein an aqueous solution of the base has the pH of preferably 8 to 14, and more preferably 11 to 12.

<19> The method as described in any one of the above-mentioned <1> to <8> and <16> to <18>, wherein the base is an inorganic base.

<20> The method as described in the above-mentioned <19>, wherein the inorganic base is an alkali metal carbonate.

<21> The method as described in the above-mentioned <20>, wherein the alkali metal carbonate is sodium carbonate.

<22> The method as described in the above-mentioned <19>, wherein the inorganic base is an alkali metal hydrogen carbonate.

<23> The method as described in the above-mentioned <22>, wherein the alkali metal hydrogen carbonate is sodium hydrogen carbonate.

<24> The method as described in the above-mentioned <19>, wherein the inorganic base is an alkali metal hydroxide.

<25> The method as described in the above-mentioned <24>, wherein the alkali metal hydroxide is sodium hydroxide.

<26> The method as described in the above-mentioned <19>, wherein the inorganic base is an alkali metal hydrogen phosphate.

<27> The method as described in the above-mentioned <26>, wherein the alkali metal hydrogen phosphate is disodium hydrogen phosphate.

<28> The method as described in any one of the above-mentioned <1> to <8> and <16> to <18>, wherein the base is an organic base.

<29> The method as described in the above-mentioned <28>, wherein the organic base is triethylamine or 4-dimethylaminopyridine.

<30> The method as described in any one of the above-mentioned <1> to <8> and <16> to <18>, wherein the base is a metal alkoxide.

<31> The method as described in the above-mentioned <30>, wherein the metal alkoxide is sodium methoxide or sodium ethoxide.

<32> The method as described in any one of the above-mentioned <1> to <8> and <16> to <18>, wherein the base is an alkyl metal.

<33> The method as described in any one of the above-mentioned <1> to <32>, wherein the treatment process is performed in the presence of an alcohol.

<34> The method as described in the above-mentioned <33>, wherein the alcohol is methanol or ethanol.

<35> The method as described in the above-mentioned <33> or <34>, wherein the use amount of the alcohol is preferably 1 to 50 mass %, more preferably 5 to 20 mass %, and further preferably 8 to 15 mass % with respect to a reaction solution after the reaction, a solution of the organic layer after the reaction, or a solution obtained by re-dissolution in an organic solvent after the isolation.

<36> The method as described in any one of the above-mentioned <1> to <35>, wherein the addition amount of the acid or base used in the treatment process is preferably 1 to 50 mass %, and more preferably 5 to 20 mass % with respect to a reaction solution after the reaction, a solution of the organic layer after the reaction, or a solution obtained by re-dissolution in an organic solvent after the isolation.

<37> The method as described in any one of the above-mentioned <1> to <36>, wherein the temperature in the treatment process is preferably 0 to 100° C., more preferably 1 to 90° C., even more preferably 20 to 80° C., and further preferably 40 to 70° C.

<38> The method as described in any one of the above-mentioned <1> to <37>, wherein the time in the treatment process is preferably 1 to 15 hours, more preferably 3 to 15 hours, even more preferably 3 to 10 hours, and further preferably 3 to 5 hours.

<39> The method as described in any one of the above-mentioned <4> and <8> to <38>, wherein the carbonyl compound is a compound represented by the formula (5) described below.

$$\underset{R_a}{\overset{O}{\underset{\|}{C}}}R_b \tag{5}$$

wherein $R_a$ and $R_b$ each represent independently, a hydrogen atom or an organic group, with the proviso that $R_a$ and $R_b$ are not a hydrogen atom at the same time.

<40> The method as described in the above-mentioned <39>, wherein $R_a$ is a substituted or unsubstituted aliphatic hydrocarbon group, and $R_b$ is a hydrogen atom or a substituted or unsubstituted aliphatic hydrocarbon group.

<41> The method as described in the above-mentioned <39> or <40>, wherein $R_a$ is a substituted or unsubstituted alkenyl group, and $R_b$ is a hydrogen atom.

<42> The method as described in the above-mentioned <41>, wherein the carbon number of the alkenyl group is preferably 2 to 32, and more preferably 5 to 30.

<43> The method as described in any one of the above-mentioned <39> to <42>, wherein $R_a$ is a 2-methylbuta-1,3-dienyl group, a 6-methyleneocta-2,7-dien-2-yl group, a 6-methylocta-2,5,7-trien-2-yl group, a 6,10,15,19,23-pentamethyltetracosa-2,6,10,14,18,22-hexaen-2-yl group, a 2,6,10-trimethylundeca-1,5,9-trienyl group, a 4-(4-methoxy-2,3,6-trimethylphenyl)-2-methylbuta-1,3-dienyl group, or a 4-(2,6,6-trimethyl-1-cyclohexenyl)-2-methylbuta-1,3-dienyl group.

<44> (2E,4E,6E,10E)-3,7,11,15-tetramethylhexadeca-2,4,6,10,14-pentaenoic acid that is substantially free of tetraethyl pyrophosphate.

<45> A pharmaceutical composition comprising (2E,4E,6E,10E)-3,7,11,15-tetramethylhexadeca-2,4,6,10,14-pentaenoic acid as described in the above-mentioned <44>.

<46> The pharmaceutical composition as described in the above-mentioned <45>, wherein the dosage form is a tablet, a capsule, a pill, a powder, a granule, a subtle granule, a dry syrup, an oral jelly, an oral solution or a syrup.

EXAMPLES

The present invention will be further specifically described with Examples below, but the scope of the present invention is not limited to the Examples described below. Meanwhile, the analysis conditions in Examples are as described below.

<Analysis Condition>

The purities of TEMPC and TEPP, and the content of TEMPC were measured with the conditions described below using gas chromatography. The conditions are as described below.

Apparatus: GC-2010 manufactured by Shimadzu Corporation
Detector: Hydrogenation ionization detector
Column: Ultra1 manufactured by Agilent (25 m×0.32 mm I.D. df=0.52 µL)
Column temperature: Elevated to 280° C. from 150° C. at 10° C. per minute, and kept at 280° C. for 2 minutes
Inlet temperature: Set up to 300° C.
Detector temperature: Set up to 300° C.

Method for measuring purities of TEMPC and TEPP

A solution of TEMPC/monochlorobenzene was taken as a sample solution. Analysis was performed with the above-mentioned conditions with respect to 0.2 µL of the sample solution, and the peak areas of TEMPC and TEPP were measured by the automatic integration method, and obtained by the area percentage method.

Method for Measuring Content of TEMPC 1.0 g of a TEMPC/monochlorobenzene solution was weighed precisely, and monochlorobenzene was added to make exactly 10 mL, which was taken as a sample solution. 0.1 g, 0.3 g and 0.5 g of TEMPC (reagent manufactured by Wako Pure Chemical Industries, Ltd.), were weighed precisely, and monochlorobenzene was added to make exactly 20 mL, which was taken as the standard solution. Analysis was performed with the above-mentioned conditions with respect to 1 µL of the sample solution and the standard solution, respectively, and the peak area of TEMPC was measured by the automatic integration method, and obtained by external standard method.

Method for Calculating Content of TEPP

The content of TEPP was calculated by the equation described below.

Content of $TEPP(g)$=Content of $TEMPC(g)$×purity of $TEPP(\%)$

Synthesis Example 1

Synthesis of TEMPC

To a 3000 mL four-neck flask equipped with a thermometer and a condenser tube, 440 g of triethyl phosphite was put in, and the flask was heated to 110° C. of internal temperature with use of an oil bath. To this, 1500 g (90% GC purity) of ethyl 4-bromo-3-methylcrotonate/monochlorobenzene solution was dropped over 100 minutes. After completion of the dropping, the reaction solution was reacted at 110 to at 120° C. of the internal temperature for 3 hours, whereby to give 1700 g of a TEMPC/monochlorobenzene solution in 81% GC purity.

Example 1

With respect to 50 g of the TEMPC/monochlorobenzene solution obtained in Synthesis Example 1 (content of TEMPC: 13 g, content of TEPP: 0.083 g), 2.5 g (5 weight %) of 5% aqueous solution of sulfuric acid was added, and stirring was performed at 25° C. for 3 hours. The obtained solution was analyzed with gas chromatography, and the contents of TEMPC and TEPP were measured. The TEMPC decomposition rate and the TEPP removal rate, which are calculated from each of the contents before and after the treatment, are represented in Table 1.

Examples 2 to 29

Similar manipulations to those of Example 1 were performed except that the kind, the concentration and the treatment temperature of the acid or base were changed to those represented in Tables 1 to 2, and analysis was performed with respect to the obtained solution. The results thereof are represented in Tables 1 or 2 together with those of Example 1.

Reference Example 1

Similar manipulations to those of Example 1 were performed except that water instead of the acid or base was used for the treatment, and analysis was performed with respect to the obtained solution. The results thereof are represented in Table 2.

Comparative Example 1

195 g of the TEMPC/monochlorobenzene solution (content of TEMPC: 53 g, content of TEPP: 0.1 g) obtained in Synthesis Example 1 was purified with simple distillation (temperature: 145° C., pressure: 0.01 kPa). Analysis was performed with respect to the purified TEMPC, and as a result, the TEPP removal rate was 10%. In addition, the recovery rate of TEMPC was 43%.

TABLE 1

| Example | Acid used Kind | Concentration | pH | Addition amount (mass %) | Treatment temperature | Removal rate of TEPP (%) | Decomposition rate of TEMPC (%) |
|---|---|---|---|---|---|---|---|
| 1 | Sulfuric acid | 5% aqueous solution | 1 | 5 | 25° C. | 97.0 | 4.3 |
| 2 | Sulfuric acid | 5% aqueous solution | 1 | 5 | 40° C. | 97.2 | 3.9 |
| 3 | Sulfuric acid | 5% aqueous solution | 1 | 5 | 60° C. | 96.9 | 3.9 |
| 4 | Sulfuric acid | 85% aqueous solution | 1 | 5 | 25° C. | 97.0 | 7.5 |
| 5 | Sulfuric acid | 85% aqueous solution | 1 | 5 | 40° C. | 97.2 | 8.2 |
| 6 | Sulfuric acid | 85% aqueous solution | 1 | 5 | 60° C. | 97.6 | 7.1 |
| 7 | Sulfuric acid | 1% aqueous solution | 1 | 50 | 60° C. | 83.0 | 8.9 |
| 8 | Phosphoric acid | 85% aqueous solution | 1 | 5 | 60° C. | 97.4 | 6.7 |
| 9 | Acetic acid | 100% | 1 | 5 | 60° C. | 96.8 | 7.5 |
| 10 | Sulfuric acid | 5% aqueous solution + Ethanol (weight ratio = 1:3) | 1 | 20 | 60° C. | 97.0 | 7.5 |

TABLE 2

| Example | Base used Kind | Concentration | pH | Addition amount (mass %) | Treatment temperature | Removal rate of TEPP (%) | Decomposition rate of TEMPC (%) |
|---|---|---|---|---|---|---|---|
| 11 | Sodium hydroxide | 2% aqueous solution | 12 | 5 | 60° C. | 95.3 | 7.9 |
| 12 | Sodium hydroxide | 3% aqueous solution | 12 | 5 | 60° C. | 95.2 | 9.8 |
| 13 | Sodium hydroxide | 4% aqueous solution | 12 | 5 | 60° C. | 95.9 | 7.8 |
| 14 | Sodium hydroxide | 5% aqueous solution | 12 | 5 | 60° C. | 95.6 | 9.2 |
| 15 | Sodium hydroxide | 10% aqueous solution | 12 | 2.5 | 60° C. | 95.9 | 10.5 |
| 16 | Sodium hydroxide | 10% aqueous solution | 12 | 5 | 60° C. | 96.2 | 9.2 |
| 17 | Sodium hydroxide | 10% aqueous solution | 12 | 10 | 60° C. | 94.9 | 9.8 |
| 18 | Sodium hydroxide | 25% aqueous solution | 12 | 5 | 25° C. | 97.8 | 9.4 |
| 19 | Sodium hydroxide | 25% aqueous solution | 12 | 5 | 40° C. | 97.9 | 9.9 |
| 20 | Sodium hydroxide | 25% aqueous solution | 12 | 5 | 60° C. | 95.2 | 16.4 |
| 21 | Sodium carbonate | 5% aqueous solution | 11 | 50 | 25° C. | 95.2 | 8.9 |

TABLE 2-continued

| | Base used | | | | | Removal | |
|---|---|---|---|---|---|---|---|
| Example | Kind | Concentration | pH | Addition amount (mass %) | Treatment temperature | rate of TEPP (%) | Decomposition rate of TEMPC (%) |
| 22 | Sodium carbonate | 5% aqueous solution | 11 | 50 | 40° C. | 95.9 | 10.3 |
| 23 | Sodium carbonate | 5% aqueous solution | 11 | 50 | 60° C. | 96.2 | 10.7 |
| 24 | Sodium hydrogen carbonate | 5% aqueous solution | 8 | 50 | 60° C. | 90 | 9.7 |
| 25 | Disodium hydrogen phosphate | 5% aqueous solution | 9 | 50 | 60° C. | 94.1 | 8.2 |
| 26 | Triethyl amine | 5% aqueous solution | 11 | 50 | 60° C. | 90.9 | 6.6 |
| 27 | 4-Dimethylamino pyridine | 5% aqueous solution | 11 | 5 | 60° C. | 93.9 | 8.9 |
| 28 | Sodium methoxide | 10% methanol solution | 12 | 5 | 60° C. | 95.2 | 2.6 |
| 29 | Sodium ethoxide | 5% ethanol solution | 12 | 50 | 60° C. | 93.6 | 9.3 |
| Reference Example 1 | Water | — | 7 | 50 | 60° C. | 83.6 | 11.9 |

Example 30

Synthesis of (2E,4E,6E,10E)-3,7,11,15-tetramethyl-hexadeca-2,4,6,10,14-pentaenoate ethyl Sodium ethoxide (4.2 g) was added to N,N-dimethyl formamide (35 mL) under nitrogen atmosphere, and the reaction solution was cooled to −20° C., and then the solution of TEMPC (16.5 g) in N,N-dimethyl formamide (10 mL) manufactured by the treatment at the conditions of Example 6 was slowly added, and the reaction solution was stirred at −20° C. for 20 minutes. To this, a solution of farnesal (11.5 g) in N,N-dimethylformamide (10 mL) was added, and the reaction solution was stirred for 10 minutes at the same temperature. After the reaction, the reaction solution was dropped to 10% ammonium chloride solution (50 mL) cooled to 0° C., and extracted with n-heptane. The organic layer was washed with 10 mL methanol/3 mL water, and 10 mL methanol/3 mL water, and further washed twice with 10 mass % of sodium chloride solution (15 mL). The organic layer was concentrated under reduced pressure, to give 17.0 g of ethyl (2E,4E,6E,10E)-3,7,11,15-tetramethyl-hexadeca-2,4,6,10,14-pentaenoate.

Example 31

Synthesis of (2E,4E,6E,10E)-3,7,11,15-tetramethyl-hexadeca-2,4,6,10,14-pentaenoic acid Potassium hydroxide (4.30 g) was dissolved in 2-propanol (40 mL) under nitrogen atmosphere, and the reaction solution was heated to 70° C., and then ethyl (2E,4E,6E,10E)-3,7,11,15-tetramethyl-2,4,6,10,14-hexadecapentaenoate (17.0 g)/2-propanol (30 mL) was dropped thereto. After 15 minutes, the reaction solution was cooled to 0° C., and poured into cold water (70 mL). The reaction solution was washed with n-heptane (40 mL and 25 mL) sequentially, and the aqueous layer was pH-adjusted with diluted hydrochloric acid (26 mL), and then toluene (50 mL) was added thereto and an organic layer was extracted. The organic layer was washed with 5 mass % sodium chloride solution (50 mL×twice), and concentrated under reduced pressure. When the distillation of toluene receded, methanol (20 mL) was added to the organic layer and concentrated under reduced pressure. Methanol (25 mL) was further added and dissolved, and the solution was cooled to crystallization. Once the internal temperature was elevated to 56° C., then the solution was cooled again to 0° C. to crystallization, and taken by filtration to give a wet crude crystal of (2E,4E,6E,10E)-3,7,11,15-tetramethylhexadeca-2,4,6,10,14-pentaenoic acid (9.07 g, 8.80 g in conversion to a dry crude crystal).

(2E,4E,6E,10E)-3,7,11,15-tetramethyl-2,4,6,10,14-hexadecapentaenoic acid (9.04 g wet crude crystal) was added to methanol (50 mL) under nitrogen atmosphere, and dissolved by heating to 60° C. This was filtered, and then cooled to crystallization. The precipitated crystal was taken by filtration to give (2E,4E,6E,10E)-3,7,11,15-tetramethylhexadeca-2,4,6,10,14-pentaenoic acid (8.15 g wet crystal). This was dried under reduced pressure to give a purified product of (2E,4E,6E,10E)-3,7,11,15-tetramethylhexadeca-2,4,6,10,14-pentaenoic acid (7.70 g). Residual TEPP was not recognized in this.

1H-NMR (CD$_3$OD) δ (ppm); 1.59 (3H, s), 1.61 (3H, s), 1.66 (3H, d, J=0.7 Hz), 1.85 (3H, d, J=0.6 Hz), 1.97 (2H, m), 2.06 (2H, m), 2.16 (2H, m), 2.16 (2H, m), 2.29 (3H, d, J=1.0 Hz), 5.08 (1H, m), 5.11 (1H, m), 5.74 (1H, s), 5.98 (1H, d, J=11.0 Hz), 6.22 (1H, d, J=15.2 Hz), 6.91 (1H, dd, J=11.0, 15.2 Hz).

Example 32

Soft Capsule (1)

The peretinoin obtained according to Examples 30 and 31 can be prepared as a soft capsule containing 75 to 150 mg of the peretinoin according to the method described in the pamphlet of International Publication No. WO2004/017958.

Example 33

Soft Capsule (2)

The tretinoin obtained according to Examples 30 and 31 can be prepared as a soft capsule containing 10 mg of tretinoin using 10 mg tretinoin, bees wax, hydrogenated oil and soybean oil as the content fillers, and gelatin, glycerin, titanium oxide, yellow ferric oxide, ferric oxide, D-sorbitol, D-mannitol, hydrogenated oligosaccharide as the coating by the method in accordance with Example 32.

Example 34

Hard Capsule (1)

A capsule containing 10 mg etretinate can be prepared by mixing 10 mg etretinate obtained according to Examples 30 and 31, crystalline cellulose, tocopherol, gelatin and dextrin, and filling the obtained mixture into a No. 4 capsule.

Example 35

Hard Capsule (2)

A capsule containing 25 mg etretinate can be prepared by mixing 25 mg etretinate obtained according to Examples 30 and 31, crystalline cellulose, povidone, tocopherol, gelatin and dextrin, and filling the obtained mixture into a No. 2 capsule.

By the manufacturing method of the present invention, it is possible to manufacture triethyl-3-methyl-4-phosphonocrotonate with lowered content of tetraethyl pyrophosphate that is an impurity. Furthermore, by using triethyl-3-methyl-4-phosphonocrotonate manufactured by the present manufacturing method, it is possible to manufacture a medicine, an agricultural chemical and an industrial product with excellent quality.

The invention claimed is:

1. A method for manufacturing a compound of Formula (III), the method comprising:
reacting a compound of Formula (I) with a compound of Formula (II) to obtain a reaction product; and
contacting the reaction product with (i) at least one acid selected from the group consisting of hydrochloric acid, sulfuric acid, nitric acid, phosphoric acid, nitrous acid, trifluoroacetic acid, oxalic acid, formic acid, acetylacetic acid, lactic acid, succinic acid, benzoic acid, adipic acid, acetic acid, and propionic acid, or (ii) a base, thereby obtaining the compound of Formula (III),

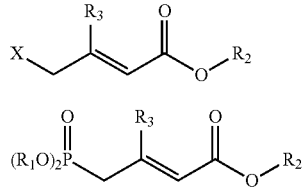

wherein
each $R_1$ is independently a $C_{1-6}$ linear or branched alkyl group that optionally is substituted by a $C_{6-10}$ aryl group, a $C_{2-6}$ linear or branched alkenyl group that optionally is substituted by a $C_{6-10}$ aryl group, a $C_{2-6}$ linear or branched alkynyl group that optionally is substituted by a $C_{6-10}$ aryl group, or a $C_{6-10}$ aryl group, $R_2$ is a hydrogen atom, or a $C_{1-6}$ linear or branched alkyl group that optionally is substituted by a $C_{6-10}$ aryl group,
$R_3$ is a $C_{1-6}$ linear or branched alkyl group, a $C_{6-10}$ aryl group, or a halogen atom, and
X is a halogen atom.

2. The method according to claim 1, wherein said contacting comprises:
(A) reacting the compound of Formula (I) with the compound of Formula (II) in the presence of the acid or the base, or
(B) reacting the compound of Formula (I) with the compound of Formula (II), followed by a treatment with the acid or the base.

3. The method according to claim 1, wherein
the compound of Formula (I) is triethyl phosphite,
the compound of Formula (II) is ethyl 4-bromo-3-methylcrotonate, and
the compound of Formula (III) is triethyl-3-methyl-4-phosphonocrotonate.

4. A method for manufacturing a compound comprising a 3-methylpenta-2,4-dienoic acid residue, the method comprising:
reacting a compound of Formula (I) with a compound of Formula (II) to obtain a reaction product;
contacting the reaction product with (i) at least one acid selected from the group consisting of hydrochloric acid, sulfuric acid, nitric acid, phosphoric acid, nitrous acid, trifluoroacetic acid, oxalic acid, formic acid, acetylacetic acid, lactic acid, succinic acid, benzoic acid, adipic acid, acetic acid, and propionic acid, or (ii) a base, to obtain a compound of Formula (III); and
subsequently reacting the compound of Formula (III) with a carbonyl compound, (R₁O)₃P     (I)

(II)

(III)

wherein
each $R_1$ is independently a $C_{1-6}$ linear or branched alkyl group that optionally is substituted by a $C_{6-10}$ aryl group, a $C_{2-6}$ linear or branched alkenyl group that optionally is substituted by a $C_{6-10}$ aryl group, a $C_{2-6}$ linear or branched alkynyl group that optionally is substituted by a $C_{6-10}$ aryl group, or a $C_{6-10}$ aryl group,
X is a halogen atom,
$R_2$ is a hydrogen atom, or a $C_{1-6}$ linear or branched alkyl group that optionally is substituted by a $C_{6-10}$ aryl group, and
$R_3$ is a $C_{1-6}$ linear or branched alkyl group, a $C_{6-10}$ aryl group, or a halogen atom.

5. The method according to claim 4, wherein
the compound of Formula (III) is triethyl-3-methyl-4-phosphonocrotonate,
the carbonyl compound is farnesal, and
the compound comprising a 3-methylpenta-2,4-dienoic acid residue is (2E,4E,6E,10E)-3,7,11,15-tetramethylhexadeca-2,4,6,10,14-pentaenoic acid.

6. The method according to claim 4, wherein
the compound of Formula (III) is triethyl-3-methyl-4-phosphonocrotonate,
the carbonyl compound is β-ionylidene acetaldehyde, and
the compound comprising a 3-methylpenta-2,4-dienoic acid residue is (2E,4E,6E,8E)-3,7-dimethyl-9-(2,6,6-trimethyl-1-cyclohexene-1-yl)nona-2,4,6,8-tetraenoic acid.

7. The method according to claim 4, wherein
the compound of Formula (III) is triethyl-3-methyl-4-phosphonocrotonate,
the carbonyl compound is (2E,4E)-5-(4-methoxy-2,3,6-trimethylphenyl)-3-methylpenta-2,4-dienal, and
the compound comprising a 3-methylpenta-2,4-dienoic acid residue is ethyl (2E,4E,6E,8E)-9-(4-methoxy-2,3,6-trimethylphenyl)-3,7-dimethylnona-2,4,6,8-tetraenoate.

8. The method according to claim 1, comprising contacting the reaction product with the acid, wherein the acid is an inorganic acid.

9. The method according to claim 8, wherein the inorganic acid is sulfuric acid or phosphoric acid.

10. The method according to claim 1, comprising contacting the reaction product with the acid, wherein the acid is an organic acid.

11. The method according to claim 10, wherein the organic acid is acetic acid.

12. The method according to claim 1, comprising contacting the reaction product with the base, wherein the base is an inorganic base.

13. The method according to claim 12, wherein the inorganic base is an alkali metal carbonate.

14. The method according to claim 13, wherein the alkali metal carbonate is sodium carbonate.

15. The method according to claim 12, wherein the inorganic base is an alkali metal hydrogen carbonate.

16. The method according to claim 15, wherein the alkali metal hydrogen carbonate is sodium hydrogen carbonate.

17. The method according to claim 12, wherein the inorganic base is an alkali metal hydroxide.

18. The method according to claim 17, wherein the alkali metal hydroxide is sodium hydroxide.

19. The method according to claim 12, wherein the inorganic base is an alkali metal hydrogen phosphate.

20. The method according to claim 19, wherein the alkali metal hydrogen phosphate is disodium hydrogen phosphate.

21. The method according to claim 1, comprising contacting the reaction product with the base, wherein the base is an organic base.

22. The method according to claim 21, wherein the organic base is triethylamine or 4-dimethylaminopyridine.

23. The method according to claim 1, comprising contacting the reaction product with the base, wherein the base is a metal alkoxide.

24. The method according to claim 23, wherein the metal alkoxide is sodium methoxide or sodium ethoxide.

25. The method according to claim 1, comprising contacting the reaction product with the base, wherein the base is an alkyl metal.

26. The method according to claim 1, wherein said contacting occurs in the presence of an alcohol.

27. The method according to claim 26, wherein the alcohol is methanol or ethanol.

28. The method according to claim 4, wherein the carbonyl compound is a compound of Formula (V):

$$R_a \overset{O}{\underset{}{\|}} R_b \quad (V)$$

wherein $R_a$ and $R_b$ each independently represent a hydrogen atom or an organic group, with the proviso that $R_a$ and $R_b$ are not simultaneously a hydrogen atom.

29. The method according to claim 28, wherein
$R_a$ is a substituted or an unsubstituted aliphatic hydrocarbon group, and
$R_b$ is a hydrogen atom or a substituted or an unsubstituted aliphatic hydrocarbon group.

30. The method according to claim 2, wherein
the compound of Formula (I) is triethyl phosphite,
the compound of Formula (II) is ethyl 4-bromo-3-methylcrotonate, and
the compound of Formula (III) is triethyl-3-methyl-4-phosphonocrotonate.

31. The method according to claim 4, comprising contacting the reaction product with the base, wherein
the base is an inorganic or organic base, a metal alkoxide, or an alkyl metal.

32. The method according to claim 4, wherein the contacting of the reaction product with the acid or the base is performed in the presence of an alcohol.

33. The method according to claim 1, comprising contacting the reaction product with the base.

34. The method according to claim 1, comprising contacting the reaction product with the acid.

35. The method according to claim 1, wherein the compound of Formula (III) is obtained with a residual ratio of pyrophosphoric acid ester of less than 5%.

36. The method according to claim 1, wherein the amount of acid or base is 1 to 50% by mass with respect to a reaction solution after the reaction, a solution of an organic layer after the reaction, or a solution obtained by re-dissolution in an organic solvent after isolation of the compound of Formula (III).

37. The method according to claim 4, wherein the amount of acid or base is 1 to 50% by mass with respect to a reaction solution after the reaction, a solution of an organic layer after the reaction, or a solution obtained by re-dissolution in an organic solvent after isolation of the compound of Formula (III).

* * * * *